(12) United States Patent
Chang et al.

(10) Patent No.: US 12,016,936 B2
(45) Date of Patent: *Jun. 25, 2024

(54) NEOVASCULAR-TARGETING CONTRAST MEDIUM COMPOSITION AND METHOD FOR PREPARING SAME

(71) Applicant: KOREA BASIC SCIENCE INSTITUTE, Daejeon (KR)

(72) Inventors: Ki-Yuk Chang, Seoul (KR); Chan-Woo Kim, Suwon-si (KR); Kwan-Soo Hong, Cheongju-si (KR); Hyun-Seung Lee, Seo-gu (KR); Hyun-Min Kim, Gimje-si (KR)

(73) Assignee: KOREA BASIC SCIENCE INSTITUTE, Daejeon (KR)

( * ) Notice: Subject to any disclaimer, the term of this patent is extended or adjusted under 35 U.S.C. 154(b) by 531 days.

This patent is subject to a terminal disclaimer.

(21) Appl. No.: 17/262,503

(22) PCT Filed: Jul. 24, 2019

(86) PCT No.: PCT/KR2019/009147
§ 371 (c)(1),
(2) Date: Jul. 28, 2021

(87) PCT Pub. No.: WO2020/022765
PCT Pub. Date: Jan. 30, 2020

(65) Prior Publication Data
US 2022/0175976 A1 Jun. 9, 2022

(30) Foreign Application Priority Data
Jul. 25, 2018 (KR) .................. 10-2018-0086816

(51) Int. Cl.
*A61K 51/10* (2006.01)
(52) U.S. Cl.
CPC ................ *A61K 51/1027* (2013.01)
(58) Field of Classification Search
None
See application file for complete search history.

(56) References Cited

U.S. PATENT DOCUMENTS 9,694,089 B2 7/2017 Rajopadhye et al.

FOREIGN PATENT DOCUMENTS

CN 103191447 A 7/2013

OTHER PUBLICATIONS

D'Huyvetter et al. Radiolabeled nanobodies as theranostic tools in targeted radionuclide therapy of cancer. 2014 Expert Opin. Drug Deliv. 11: 1939-1954. (Year: 2014).*
Mi-Hye Hwang, et al., "Biological Production of an Integrin $\alpha\beta3$ Targeting Imaging Probe and Functional Verification", BioMed research international, 2015, pp. 1-8, vol. 2015, Article ID 681012.
Falguni Basuli, et al., "Fast indirect fluorine-18 labeling of protein/peptide using the useful 6-fluoronicotinic acid-2,3,4,6-tetrafluorophenyl prosthetic group: a method comparable to direct fluorination", Journal of Labelled Compounds and Radiopharmaceuticals, 2017, pp. 168-175, vol. 60.
Maria Elena Iezzi, et al., "Single-Domain Antibodies and the Promise of Modular Targeting in Cancer Imaging and Treatment", Frontiers in immunology, Feb. 19, 2018, pp. 1-11, vol. 9, Article 273.
International Search Report for PCT/KR2019/009147 dated Nov. 15, 2019 [PCT/ISA/210].

* cited by examiner

*Primary Examiner* — Jennifer Chin
(74) *Attorney, Agent, or Firm* — Sughrue Mion, PLLC

(57) ABSTRACT

The present invention relates to a neovascular-targeting contrast medium composition and a method for preparing same. The neovascular-targeting contrast medium composition according to the present invention exhibits high binding force to neovascularization-associated $\alpha_v\beta_3$ integrin, excellent tissue permeability and biostability, enables simple measurement in vitro, in vivo, or ex vivo, and thus is effective in the detection of neovascularization and in diagnosing diseases associated therewith, and therefore may be usefully employed in the relevant industries.

12 Claims, 3 Drawing Sheets

Specification includes a Sequence Listing.

SEQUENCE LISTING

<160> NUMBER OF SEQ ID NOS: 16

<210> SEQ ID NO 1
<211> LENGTH: 354
<212> TYPE: DNA
<213> ORGANISM: Artificial Sequence
<220> FEATURE:
<223> OTHER INFORMATION: VHH-25

<400> SEQUENCE: 1

```
gaggtgcagc tggtggagtc tgggggaggc tcggtgcagg ctggagggtc tctgagactc      60
tcctgtgtag tctctggata cacctgtagc gtctacgaca tgatctggta ccgccagcct     120
ccagggaagg agcgcgagtt cgtctcactc attaatagta atggtagaac aacctacgca     180
gactccgtga agggccgatt caccatctcc caaaacaacg ccaagaacac ggtgtatctg     240
cagatgaaca gcctgaaacc tgaggacacg gcaatgtact actgtcatgc ggcctgctat     300
tcaccctctc ggctgaatta ttggggccag gggacccagg tcactgtctc ctca            354
```

<210> SEQ ID NO 2
<211> LENGTH: 402
<212> TYPE: DNA
<213> ORGANISM: Artificial Sequence
<220> FEATURE:
<223> OTHER INFORMATION: VHH-13

<400> SEQUENCE: 2

```
catgtgcagc tggtggagtc tgggggaggc tcggtgcagc tggagagtc tctgagactc       60
tcctgtgtag cctctggata caccgtcagt agctcctgca tggcctggtt ccgccaggct     120
ccaggaaagg agcgcgaggt ggtcgcaact attgttgtta ctagtgatac gaccagcact     180
ttctatgccg actccgtaaa gggccgattc accatctccc agacaacgc caagaataca     240
ctaaatctgc aaatgaatag cctggaaccg tccgacactg ccatgtacta ctgtgcggca     300
gatcgcaagt ggaacgtttg tagtcgtggt tatcgctaca cccctaattg gccaaccaa     360
tttacgttct ggggccaggg gacccaggtc accgtctcct ca                         402
```

<210> SEQ ID NO 3
<211> LENGTH: 354
<212> TYPE: DNA
<213> ORGANISM: Artificial Sequence
<220> FEATURE:
<223> OTHER INFORMATION: VHH-22

<400> SEQUENCE: 3

```
caggtgcagc tggtggagtc tgggggaggc tcggtgcagg ctggagggtc tctgagactc      60
tcctgtgtag tctctggata cacctgtagc gtctacgaca tgatctggta ccgccagcct     120
ccagggaagg agcgcgagtt cgtctcactc attaatagta atggtagaac aacctacgca     180
gactccgtga agggccgatt caccatctcc caaaacaacg ccaagaacac ggtgtatctg     240
cagatgaaca gcctgaaacc tgaggacacg gcaatgtact actgtcatgc ggcctgctat     300
tcaccctctc ggctgaatta ttggggccag gggacccctgg tcaccgtctc ctca           354
```

<210> SEQ ID NO 4
<211> LENGTH: 402
<212> TYPE: DNA
<213> ORGANISM: Artificial Sequence
<220> FEATURE:
<223> OTHER INFORMATION: VHH-11

<400> SEQUENCE: 4

```
gatgtgcagc tggtggagtc tgggggaggc tcggtgcagc ctggagagtc tctgagactc       60
tcctgtgtag cctctggata caccgtcagt agctcctgca tggcctggtt ccgccaggct      120
ccaggaaagg agcgcgaggt ggtcgcaact attgttgtta ctagtgatac gaccagcact      180
ttctatgccg actccgtaaa gggccgattc accatctccc cagacaacgc caagaatacg      240
ctaaatctgc aaatgaatag cctggaaccg tccgacactg ccatgtacta ctgtgcggca      300
gatcgcaagt ggaacgtttg tagtcgtggt tatcgctaca cccctaattg ggccaaccaa      360
tttacgttct ggggccaggg gaccttggtc accgtctcct ca                         402
```

<210> SEQ ID NO 5
<211> LENGTH: 402
<212> TYPE: DNA
<213> ORGANISM: Artificial Sequence
<220> FEATURE:
<223> OTHER INFORMATION: VHH-17

<400> SEQUENCE: 5

```
gatgtgcagc tggtggagtc tgggggaggc tcggtgcagc ctggagagtc tctgagactc       60
tcctgtgtag cctctggata caccgtcagt agctcctgca tggcctggtt ccgccaggct      120
ccaggaaagg agcgcgaggt ggtcgcaact attgttgtta ctagtgatac gaccagcact      180
ttctatgccg actccgtaaa gggccgattc accatctccc cagacaacgc caagaatacg      240
ctaaatctgc aaatgaatag cctggaaccg tccgacactg ccatgtacta ctgtgcggca      300
gatcgcaagt ggaacgtttg tagtcgtggt tatcgctaca cccctaattg ggccaaccaa      360
tttacgttct ggggccaggg gaccttggtc accgtctcct ca                         402
```

<210> SEQ ID NO 6
<211> LENGTH: 402
<212> TYPE: DNA
<213> ORGANISM: Artificial Sequence
<220> FEATURE:
<223> OTHER INFORMATION: VHH-15

<400> SEQUENCE: 6

```
gaggtgcagc tggtggagtc tgggggaggc tcggtgcagc ctggagagtc tctgagactc       60
tcctgtgtag cctctggata caccgtcagt agctcctgca tggcctggtt ccgccaggct      120
ccaggaaagg agcgcgaggt ggtcgcaact attgttgtta ctagtgatac gaccagcact      180
ttctatgccg actccgtaaa gggccgattc accatctccc cagacaacgc caagaatacg      240
ctaaatctgc aaatgaatag cctggaaccg cccgacactg ccatgtacta ctgtgcggca      300
gatcgcaagt ggaacgtttg tagtcgtggt tatcgctaca cccctaattg ggccaaccaa      360
tttacgttct ggggccaggg gacccaggtc accgtctcct ca                         402
```

<210> SEQ ID NO 7
<211> LENGTH: 402
<212> TYPE: DNA
<213> ORGANISM: Artificial Sequence
<220> FEATURE:
<223> OTHER INFORMATION: VHH-12

<400> SEQUENCE: 7

```
gaggtgcagc tggtggagtc tgggggaggc tcggtgcagc ctggagagtc tctgagactc       60
tcctgtgtag cctctggata caccgtcagt agctcctgca tggcctggtt ccgccaggct      120
ccaggaaagg agcgcgaggt ggtcgcaact attgttgtta ctagtgatac gaccagcact      180
```

```
ttctatgccg actccgtaaa gggccgattc accatctccc cagacaacgc caagaatacg    240
ctaaatctgc aaatgaatag cctggaaccg tccgacactg ccatgtacta ctgtgcggca    300
gatcgcaagt ggaacgtttg tagtcgtggt tatcgctaca cccctaattg ggccaaccaa    360
tttacgttct ggggccaggg gacccaggtc accgtctcct ca                       402

<210> SEQ ID NO 8
<211> LENGTH: 399
<212> TYPE: DNA
<213> ORGANISM: Artificial Sequence
<220> FEATURE:
<223> OTHER INFORMATION: VHH-16

<400> SEQUENCE: 8
gatgtgcagc tggtggagtc tgggggaggc tcggtgcagc tggagggtc tctgagactc      60 tcctgtgcag cctctggata caccgtcgag aactcctgca tggcctggtt ccgccaggct    120
ccagggaagg agcgcgaggt ggtcgcaact attgttacta ataatgcgac cggtactttc    180
tatgccgact ccgtgaaggg ccgattcacc gtctcccaag acaacgccaa gaatacgcta    240
aatctgcaaa tgaatagcct ggaacctgag gacacagcca tgtactactg tgcggcagat    300
accaagtgga tagtttgtag tcgtggttat cgctacaccc ctaattgggc caaccaattt    360
aagtactggg gccaggggac ccaggtcacc gtctcctca                           399

<210> SEQ ID NO 9
<211> LENGTH: 399
<212> TYPE: DNA
<213> ORGANISM: Artificial Sequence
<220> FEATURE:
<223> OTHER INFORMATION: VHH-20

<400> SEQUENCE: 9
gatgtgcagc tggtggagtc tgggggaggc tcggtgcagc tggagggtc cctgagactc      60 tcctgtgcag cctctggata caccgtcgat aactcctgca tggcctggtt ccgccaggct    120
ccagggaagg agcgcgaggt ggtcgcaact attgttacta ataatgcgac cagcactttc    180
tatgccgact ccgtgaaggg ccgattcacc gtctcccacg acaacgccaa gaatacgcta    240
aatctgcaaa tgaataccct ggaacctgag gacactgcca tgtactactg tgcggcagat    300
accaagtgga tagtttgtag tcgtggttat cgctacaccc ctaattgggc caaccatttt    360
aattactggg gccaggggac cctggtcacc gtctcctca                           399

<210> SEQ ID NO 10
<211> LENGTH: 384
<212> TYPE: DNA
<213> ORGANISM: Artificial Sequence
<220> FEATURE:
<223> OTHER INFORMATION: VHH-23

<400> SEQUENCE: 10
catgtgcagc tggtggagtc tgggggaggc tcggtgcaga ctggagggtc tctgagactc      60
tcctgtgcag cctctggata cacctcaagt accgtctaca tggcttggtt ccgccagact    120
ccagggaagc agcgcgaggg ggtcgcagca atttatactg tggtggtcc tacatactat    180 gccgactccg tgaagggccg attcaccatc tcccaagaca cgccaagaa tacggtgtat    240 ctccaaatga cacccctgaa acctgaagac actgccatgt actactgtgc ggccgatcgc    300
tatgtgtacc ggttagttac taactggtac agaccgtctt tttatacata ctggggccag    360
gggacccagg tcaccgtctc ctca                                           384
```

<210> SEQ ID NO 11
<211> LENGTH: 118
<212> TYPE: PRT
<213> ORGANISM: Artificial Sequence
<220> FEATURE:
<223> OTHER INFORMATION: VHH-25 of amino acid

<400> SEQUENCE: 11

Glu Val Gln Leu Val Glu Ser Gly Gly Gly Ser Val Gln Ala Gly Gly
1               5                   10                  15

Ser Leu Arg Leu Ser Cys Val Val Ser Gly Tyr Thr Cys Ser Val Tyr
            20                  25                  30

Asp Met Ile Trp Tyr Arg Gln Pro Pro Gly Lys Glu Arg Glu Phe Val
        35                  40                  45

Ser Leu Ile Asn Ser Asn Gly Arg Thr Thr Tyr Ala Asp Ser Val Lys
    50                  55                  60

Gly Arg Phe Thr Ile Ser Gln Asn Asn Ala Lys Asn Thr Val Tyr Leu
65                  70                  75                  80

Gln Met Asn Ser Leu Lys Pro Glu Asp Thr Ala Met Tyr Tyr Cys His
                85                  90                  95

Ala Ala Cys Tyr Ser Pro Ser Arg Leu Asn Tyr Trp Gly Gln Gly Thr
            100                 105                 110

Gln Val Thr Val Ser Ser
        115

<210> SEQ ID NO 12
<211> LENGTH: 134
<212> TYPE: PRT
<213> ORGANISM: Artificial Sequence
<220> FEATURE:
<223> OTHER INFORMATION: VHH-13 of amino acid

<400> SEQUENCE: 12

His Val Gln Leu Val Glu Ser Gly Gly Gly Ser Val Gln Pro Gly Glu
1               5                   10                  15

Ser Leu Arg Leu Ser Cys Val Ala Ser Gly Tyr Thr Val Ser Ser Ser
            20                  25                  30

Cys Met Ala Trp Phe Arg Gln Ala Pro Gly Lys Glu Arg Glu Val Val
        35                  40                  45

Ala Thr Ile Val Val Thr Ser Asp Thr Thr Ser Thr Phe Tyr Ala Asp
    50                  55                  60

Ser Val Lys Gly Arg Phe Thr Ile Ser Pro Asp Asn Ala Lys Asn Thr
65                  70                  75                  80

Leu Asn Leu Gln Met Asn Ser Leu Glu Pro Ser Asp Thr Ala Met Tyr
                85                  90                  95

Tyr Cys Ala Ala Asp Arg Lys Trp Asn Val Cys Ser Arg Gly Tyr Arg
            100                 105                 110

Tyr Thr Pro Asn Trp Ala Asn Gln Phe Thr Phe Trp Gly Gln Gly Thr
        115                 120                 125

Gln Val Thr Val Ser Ser
    130

<210> SEQ ID NO 13
<211> LENGTH: 118
<212> TYPE: PRT
<213> ORGANISM: Artificial Sequence
<220> FEATURE:
<223> OTHER INFORMATION: VHH-22 of amino acid

<400> SEQUENCE: 13

Gln Val Gln Leu Val Glu Ser Gly Gly Gly Ser Val Gln Ala Gly Gly
1               5                   10                  15

Ser Leu Arg Leu Ser Cys Val Val Ser Gly Tyr Thr Cys Ser Val Tyr
            20                  25                  30

Asp Met Ile Trp Tyr Arg Gln Pro Pro Gly Lys Glu Arg Glu Phe Val
        35                  40                  45

Ser Leu Ile Asn Ser Asn Gly Arg Thr Thr Tyr Ala Asp Ser Val Lys
    50                  55                  60

Gly Arg Phe Thr Ile Ser Gln Asn Asn Ala Lys Asn Thr Val Tyr Leu
65                  70                  75                  80

Gln Met Asn Ser Leu Lys Pro Glu Asp Thr Ala Met Tyr Tyr Cys His
                85                  90                  95

Ala Ala Cys Tyr Ser Pro Ser Arg Leu Asn Tyr Trp Gly Gln Gly Thr
            100                 105                 110

Leu Val Thr Val Ser Ser
        115

<210> SEQ ID NO 14
<211> LENGTH: 126
<212> TYPE: PRT
<213> ORGANISM: Artificial Sequence
<220> FEATURE:
<223> OTHER INFORMATION: VHH-25 with His6 tag for purification

<400> SEQUENCE: 14

Glu Val Gln Leu Val Glu Ser Gly Gly Gly Ser Val Gln Ala Gly Gly
1               5                   10                  15

Ser Leu Arg Leu Ser Cys Val Val Ser Gly Tyr Thr Cys Ser Val Tyr
            20                  25                  30

Asp Met Ile Trp Tyr Arg Gln Pro Pro Gly Lys Glu Arg Glu Phe Val
        35                  40                  45

Ser Leu Ile Asn Ser Asn Gly Arg Thr Thr Tyr Ala Asp Ser Val Lys
    50                  55                  60

Gly Arg Phe Thr Ile Ser Gln Asn Asn Ala Lys Asn Thr Val Tyr Leu
65                  70                  75                  80

Gln Met Asn Ser Leu Lys Pro Glu Asp Thr Ala Met Tyr Tyr Cys His
                85                  90                  95

Ala Ala Cys Tyr Ser Pro Ser Arg Leu Asn Tyr Trp Gly Gln Gly Thr
            100                 105                 110

Gln Val Thr Val Ser Ser Leu Glu His His His His His
        115                 120                 125

<210> SEQ ID NO 15
<211> LENGTH: 142
<212> TYPE: PRT
<213> ORGANISM: Artificial Sequence
<220> FEATURE:
<223> OTHER INFORMATION: VHH-13 with His6 tag for purification

<400> SEQUENCE: 15

His Val Gln Leu Val Glu Ser Gly Gly Gly Ser Val Gln Pro Gly Glu
1               5                   10                  15

Ser Leu Arg Leu Ser Cys Val Ala Ser Gly Tyr Thr Val Ser Ser Ser
            20                  25                  30

Cys Met Ala Trp Phe Arg Gln Ala Pro Gly Lys Glu Arg Glu Val Val
        35                  40                  45

```
Ala Thr Ile Val Val Thr Ser Asp Thr Thr Ser Thr Phe Tyr Ala Asp
    50                  55                  60

Ser Val Lys Gly Arg Phe Thr Ile Ser Pro Asn Ala Lys Asn Thr
65                  70                  75                  80

Leu Asn Leu Gln Met Asn Ser Leu Glu Pro Ser Asp Thr Ala Met Tyr
            85                  90                  95

Tyr Cys Ala Ala Asp Arg Lys Trp Asn Val Cys Ser Arg Gly Tyr Arg
            100                 105                 110

Tyr Thr Pro Asn Trp Ala Asn Gln Phe Thr Phe Trp Gly Gln Gly Thr
        115                 120                 125

Gln Val Thr Val Ser Ser Leu Glu His His His His His His
        130                 135                 140

<210> SEQ ID NO 16
<211> LENGTH: 126
<212> TYPE: PRT
<213> ORGANISM: Artificial Sequence
<220> FEATURE:
<223> OTHER INFORMATION: VHH-16 with His6 tag for purification

<400> SEQUENCE: 16

Gln Val Gln Leu Val Glu Ser Gly Gly Gly Ser Val Gln Ala Gly Gly
1               5                   10                  15

Ser Leu Arg Leu Ser Cys Val Val Ser Gly Tyr Thr Cys Ser Val Tyr
            20                  25                  30

Asp Met Ile Trp Tyr Arg Gln Pro Pro Gly Lys Glu Arg Glu Phe Val
            35                  40                  45

Ser Leu Ile Asn Ser Asn Gly Arg Thr Thr Tyr Ala Asp Ser Val Lys
    50                  55                  60

Gly Arg Phe Thr Ile Ser Gln Asn Asn Ala Lys Asn Thr Val Tyr Leu
65                  70                  75                  80

Gln Met Asn Ser Leu Lys Pro Glu Asp Thr Ala Met Tyr Tyr Cys His
            85                  90                  95

Ala Ala Cys Tyr Ser Pro Ser Arg Leu Asn Tyr Trp Gly Gln Gly Thr
            100                 105                 110

Leu Val Thr Val Ser Ser Leu Glu His His His His His His
        115                 120                 125
```

NEOVASCULAR-TARGETING CONTRAST MEDIUM COMPOSITION AND METHOD FOR PREPARING SAME

CROSS-REFERENCE TO RELATED APPLICATIONS

This application is a National Stage of International Application No. PCT/KR2019/009147, filed Jul. 24, 2019, claiming priority to Korean Patent Application No. 10-2018-0086816 filed Jul. 25, 2018, the disclosures of which are incorporated herein by reference in their respective entireties.

INCORPORATION BY REFERENCE OF SEQUENCE LISTING

The content of the electronically submitted sequence listing, file name: Q260746_sequence listing as filed.TXT; size: 13,911 bytes; and date of creation: Jan. 21, 2021, which was filed Jan. 22, 2021, is incorporated herein by reference in its entirety.

TECHNICAL FIELD

The present disclosure relates to a neovascular-targeting contrast medium composition and a method for preparing the same.

BACKGROUND ART

A positron emission tomography (PET) device images distribution of radiopharmaceuticals injected into a living body. The PET device may image biological changes in a human body caused by a disease to provide accurate information for early diagnosis of the disease and determination of disease treatment methods. Therefore, importance of the nuclear medicine imaging device is increasing.

For most of radiopharmaceuticals used in PET, chemical technique in which molecules participating in specific metabolism in the body such as water, oxygen, carbon dioxide, glucose, and amino acids are labeled with radioactive isotopes such as [$^{18}$F] fluoride, [$^{11}$C] carbon, and oxygen or [$^{13}$N] nitrogen. For example, the radiopharmaceuticals may include [$C^{11}$] methionine, [$^{13}$N] ammonia, $H_2{}^{15}O$, and [$^{18}$F] FDG (Fluoro-deoxy glucose).

In addition, metallic radioactive isotopes emitted from radiation are also widely used in the nuclear medicine. Metallic radioisotopes used for PET based diagnosis include Cu-64, Ga-68, Zr-89, and Y-86, and metallic radioisotopes used for SPECT based diagnosis include In-111 and Tc-99m. Cu-67, Y-90, Lu-177, etc. are known as therapeutic radioisotopes that may be directly used in the treatment of tumors in addition to such nuclear medical imaging based diagnosis.

Integrin is a cell surface receptor that regulates important physiological functions of cells such as cell adhesion and migration, differentiation, and proliferation. The integrin acts as a heterodimer in which α and β subunits have non-covalent bonds, and the α and β subunits are paired to form 22 integrin families. Integrin mainly binds to extracellular matrix proteins such as vitronectin, fibronectin, collagen, laminin, vWF, and fibrinogen. However, different types of integrins have different specificities to ligands. One type of integrin may bind to several ligands simultaneously. Among them, integrin $α_vβ_3$ is expressed in most of the aggressive tumor cells among various cancers including skin cancer, prostate cancer, breast cancer, cervical cancer, colon cancer, lung cancer, gallbladder cancer, pancreatic cancer, and stomach cancer. The integrin $α_vβ_3$ is known to regulate adhesion-dependent tumor cell growth, survival and invasion to improve the malignancy of various human tumors. Recently, it has been shown that β integrin regulates intracellular signaling to act as a mediator independent of adhesion to increase tumor growth and metastasis (David A Cheresh et al., Nature Medicine 2009, 15 (10): 1163). Further, the $α_vβ_3$ integrin is not expressed in normal vascular endothelial cells, but is expressed during neovascularization of cancer cells, and is characterized by binding to a peptide having an RGD (R: arginine, G: glycine, D: aspartic acid) sequence. RGD as a tumor-selective peptide has been published to be applied to tumor treatment due to its ability to selectively bind to tumor vessels.

Angiogenesis means creation of new capillary vessels from existing blood vessels. Angiogenesis is a strictly controlled phenomenon that rarely occurs under normal physiological conditions, or occurs when the embryo develops during the development of the fertilized egg, when the wound is healed in adults, and during changes in the reproductive system in the female reproductive cycle. In adults, capillary endothelial cells do not divide relatively well, and the rate of division is usually several months to several years. Angiogenesis occurs in a complex process via the interaction of various types of cells with water-soluble factors and extracellular matrix components, and its mechanism of action has not been fully identified. The angiogenesis is responsible for several diseases.

Currently, the number of commercially available antibodies are reported to be 300,000 or more, but most of commercially available antibodies may only be observed in immobilized cells. Thus, it was not possible to observe the folding of proteins or interactions between proteins in the cell in real time. Further, the existing antibodies were too large or chemically unstable to be useful in living cells. However, antibodies derived from camelid by Hamers-Casterman in 1993 consist of only the heavy chain. This structure different from a structure of the conventional antibodies (two heavy chains and two light chains). A single domain antibody serving as a functionally complete antibody has been reported (Hamers-Casterman, C. et al. 1993. Nature 363:446-448). Existing antibodies have a size of 150 kDa, recombinant antibodies have a size of 25 kDa to 50 kDa. However, single domain antibodies derived from camels, llamas, and sharks have a size of 12 kDa to 13 kDa, and thus are the smallest antibody, and thus may easily migrate into cells (Cortez-Retamozo, V. et al. al. 2004. Cancer Res. 64:2853-2857). The single domain antibodies derived from camels, llamas, and sharks have the advantage of being easily expressed in bacteria and yeast due to its easy genetic manipulation (Arbabi-Ghahroudii, M. et al. 1997. FEBS Lett. 414:521-526). Further, the single domain antibody is highly water-soluble and stable even under extreme pH conditions and temperature conditions up to 90° C. (Dumoulin, M. et al. 2002. Protein Sciii. 11:500-515, Dumoulin, M. et al. 2003. Nature 424:783-788).

Accordingly, the present inventors identified that $α_vβ_3$ integrin targeting nanobody detects $α_vβ_3$ integrin at high stability and sensitivity, and may be usefully used to diagnose all types of cancers and cancer metastasis related to $α_vβ_3$ integrin, and has angiogenesis targeting directivity, and the contrast medium composition having the nanobody coupled thereto may effectively detect angiogenesis and diagnose the angiogenesis related diseases. In this way, the present disclosure was completed.

DISCLOSURE

Technical Problem

A purpose of the present disclosure is to provide a neovascular-targeting contrast medium composition.

Another purpose of the present disclosure is to provide a contrast medium composition for diagnosing angiogenesis-related diseases.

Yet another purpose of the present disclosure is to provide a contrast medium composition for diagnosing cancer.

Another purpose of the present disclosure is to provide a method for preparing a neovascular-targeting contrast medium.

Technical Solution

In order to achieve the purposes, the present disclosure provides a neovascular-targeting contrast medium composition containing an $\alpha_v\beta_3$ integrin targeting nanobody encoded by at least one kind of base sequence selected from the group consisting of base sequences represented by SEQ ID NOs: 1 to 10; and a probe labeled with a radioactive isotope.

Further, the present disclosure provides a contrast medium composition for diagnosing angiogenesis-related diseases, the composition containing an $\alpha_v\beta_3$ integrin targeting nanobody encoded by at least one kind of base sequence selected from the group consisting of base sequences represented by SEQ ID NOs: 1 to 10; and a probe labeled with a radioactive isotope.

Further, the present disclosure provides a contrast medium composition for diagnosing cancers, the composition containing an $\alpha_v\beta_3$ integrin targeting nanobody encoded by at least one kind of base sequence selected from the group consisting of base sequences represented by SEQ ID NOs: 1 to 10; and a probe labeled with a radioactive isotope.

Furthermore, the present disclosure provides a method for preparing a neovascular-targeting contrast medium, the method including a step (step 1) of reacting an $\alpha_v\beta_3$ integrin targeting nanobody encoded by at least one kind of base sequence selected from the group consisting of base sequences represented by SEQ ID NOs: 1 to 10, and a probe labeled with a radioactive isotope in a buffer solution at pH 8.0 or higher:

[Reaction Formula 1]

(In the Reaction Formula 1, each of $R^1$ to $R^5$ represents hydrogen or halogen, $R^6$ represents C-11, N-13, O-15, F-18, Ru-82, Ga-68, Cu-60, Cu-61, Cu-62, Cu-64, Cu-67, K-38, Rb-82, Sc-44, I-123, I-124, I-125, Zr-89, Y-86, Y-90, Lu-177, In-111 or Tc-99m).

Technical Effect

The neovascular-targeting contrast medium composition according to the present disclosure exhibits high binding power to $\alpha_v\beta_3$ integrin related to angiogenesis, excellent tissue permeability and biostability, and may be easily measured in vitro, in vivo or ex vivo, and thus may be effective in detecting the angiogenesis and diagnosing angiogenesis related diseases, and thus may be usefully used in related industries.

MODES OF THE INVENTION

Hereinafter, the present disclosure will be described in detail.

Neovascular-Targeting Contrast Medium Composition

The present disclosure provides a neovascular-targeting contrast medium composition containing an $\alpha_v\beta_3$ integrin targeting nanobody encoded by at least one kind of base sequence selected from the group consisting of base sequences represented by SEQ ID NOs: 1 to 10; and a probe labeled with a radioactive isotope.

The term "integrin" in the present disclosure refers to a receptor molecule that exists on the cell surface and acts when cells adhere to extracellular matrix such as fibronectin and collagen. The integrin refers to a transmembrane glycoprotein composed of heterodimers of two subunits, that is, $\alpha$ and $\beta$ subunits. The existence of 21 types of integrins has been revealed so far. Among them, $\alpha_v\beta_3$ integrin has been reported to play a very important role in maintaining the structure of the cardiovascular system and bone tissue.

The term "nanobody" in the present disclosure refers to an antibody in which a CDR is a portion of a single domain polypeptide, and includes heavy chain antibodies, antibodies naturally devoid of light chains, single domain antibodies derived from conventional 4-chain antibodies, engineered antibodies and single domain scaffolds other than those derived from antibodies. In order to distinguish the nanobody from the VH of the 4-chain immunoglobulin, the nanobody is referred to as a variable region of a heavy chain antibody (VHH), a single-domain antibody, or an sdAb.

The nanobody according to the present disclosure refers to a naturally occurring single domain antibody derived from a heavy chain naturally free of a light chain, and acts as a specific antibody to $\alpha_v\beta_3$ integrin, and has a molecular weight of about 14 KDa to 15 KDa. The nanobody according to the present disclosure is an antibody that is a VHH derived from Camelidae, and may be derived from camels, dromedaries, llama, alpaca and wild llama. To achieve the goal of targeting $\alpha_v\beta_3$ integrin related to angiogenesis, species other than Camelidae may naturally produce the nanobody as heavy chain antibodies without light chains. However, the present disclosure is not limited thereto.

The nanobody according to the present disclosure is about 10 times smaller than an IgG molecule and is very stable as single polypeptides and are stable under extreme pH and temperature conditions. Further, the nanobody is resistant to the action of proteases, unlike conventional antibodies. When expressed in vitro, mass production of the nanobody may be realized at a high yield.

The base sequence represented by SEQ ID NO: 1 encodes the amino acid sequence of the nanobody represented by SEQ ID NO: 11. The base sequence represented by SEQ ID NO: 2 encodes the amino acid sequence thereof represented by SEQ ID NO: 12. The base sequence represented by SEQ ID NO: 3 may encode the amino acid sequence thereof represented by SEQ ID NO: 13. Further, the amino acid sequences containing the His6 tag in SEQ ID NOs: 1, 2 or 3 may be represented by amino acids of SEQ ID NOs: 14, 15 and 16, respectively.

In an embodiment of the present disclosure, in the probe labeled with the radioactive isotope, the radioactive isotope may include one of C-11, N-13, 0-15, F-18, Ru-82, Ga-68, Cu-60, Cu-61, Cu-62, Cu-64, Cu-67, K-38, Rb-82, Sc-44, I-123, I-124, 1-125, Zr-89, Y-86, Y-90, Lu-177, In-111 and Tc-99m. Preferably, the probe may be a compound represented by a following Chemical Formula 1.

[Chemical Formula 1]

(In the Chemical Formula 1, each of $R^1$ to $R^5$ represents hydrogen or halogen, $R^6$ represents C-11, N-13, O-15, F-18, Ru-82, Ga-68, Cu-60, Cu-61, Cu-62, Cu-64, Cu-67, K-38, Rb-82, Sc-44, I-123, I-124, I-125, Zr-89, Y-86, Y-90, Lu-177, In-111 or Tc-99m).

More preferably, the radioactive isotope-labeled probe may include a compound represented by a following Chemical Formula 2.

[Chemical Formula 2]

Contrast Medium Composition for Diagnosing Angiogenesis-Related Disease

Further, the present disclosure provides a contrast medium composition for diagnosing angiogenesis-related diseases, the composition containing an $\alpha_v\beta_3$ integrin targeting nanobody encoded by at least one kind of base sequence selected from the group consisting of base sequences represented by SEQ ID NOs: 1 to 10; and a probe labeled with a radioactive isotope.

In one embodiment of the present disclosure, the contrast medium composition may be used for positron emission tomography (PET) imaging, computed tomography (CT) imaging, single-photon emission computed tomography (SPEC) imaging, PET/CT imaging, PET/MRI imaging, or PET/optical imaging, PET/MR/optical imaging.

In one embodiment of the present disclosure, the angiogenesis-related disease may include at least one kind selected from the group consisting of arteriosclerosis, cancer, diabetic retinopathy, angiogenesis glaucoma, posterior lens fibrosis, proliferative vitreous retinopathy, immature retinopathy, ophthalmic inflammation, corneal ulcer, conical cornea, macular degeneration, Sjogren's syndrome, myopic tumor, corneal graft rejection, abnormal wound union, trachoma, bone disease, rheumatoid arthritis, osteoarthritis, septicemia arthritis, hemangiomas, angiofibroma, psoriasis, pyogenic granuloma, proteinuria, abdominal aortic aneurysm disease, degenerative cartilage loss due to traumatic joint damage, neuro demyelination disease, liver cirrhosis, glomerular disease, immature rupture of the embryonic membrane, inflammatory bowel disease, periodontal ligament disease, restenosis, inflammation of the central nervous system, Alzheimer's disease, skin aging, thyroid hyperplasia, and Grave's disease.

Contrast Medium Composition for Diagnosing Cancers

Further, the present disclosure provides a contrast medium composition for diagnosing cancers, the composition containing an $\alpha_v\beta_3$ integrin targeting nanobody encoded by at least one kind of base sequence selected from the group consisting of base sequences represented by SEQ ID NOs: 1 to 10; and a probe labeled with a radioactive isotope.

In one embodiment of the present disclosure, the cancer may be at least one kind selected from the group consisting of skin cancer, prostate cancer, breast cancer, cervical cancer, colon cancer, lung cancer, gallbladder cancer, pancreatic cancer, gastric cancer, ovarian cancer, malignant melanoma, malignant lymphoma, thyroid cancer, metastatic brain tumor and brain glioma.

Method for Preparing Neovascular-Targeting Contrast Medium

Furthermore, the present disclosure provides a method for preparing a neovascular-targeting contrast medium, the method including a step (step 1) of reacting an $\alpha_v\beta_3$ integrin targeting nanobody encoded by at least one kind of base sequence selected from the group consisting of base sequences represented by SEQ ID NOs: 1 to 10, and a probe labeled with a radioactive isotope in a buffer solution at pH 8.0 or higher:

[Reaction Formula 1]

In the method for preparing the neovascular-targeting contrast medium acceding to the present disclosure, the step 1 is characterized in that the buffer solution having a pH of 8.0 or higher is an amine-free buffer. Preferably, the buffer solution may include sodium bicarbonate ($NaHCO_3$) aqueous solution, Tris buffer, and phosphate buffer.

EXAMPLES

Hereinafter, the present disclosure will be described in more detail based on following Examples. However, the following Examples are only to illustrate the present disclosure, and the content of the present disclosure is not limited to the following Examples.

<Example 1> Preparation of Neovascular-Targeting Contrast Medium

Synthesis of 2,3,5,6-tetrafluorophenyl-6-[$^{18}$F]-fluoronicotinate) was made using a known method.
2,3,5,6-tetrafluorophenyl-6-[$^{18}$F]-fluoronicotinate 86 mCi (millicurie) and 0.5 mg of nanobody reacted with each other in 0.2 ml of 0.1M concentration of sodium bicarbonate ($NaHCO_3$) aqueous solution at room temperature for 10 minutes. After removing the unreacted material using a size exclusion column (PD-10, GE Healthcare), a final 43 mCi $^{18}$F-nanobody was prepared.
$^{18}$F-nanobodeis were prepared using nanobodies containing Lysine and His6 tags in base sequence SEQ ID No: 1, respectively and abbreviated as Nbs-#1 and Nbs-#2, respectively.

Table 1 shows the results of identifying the radioactivity of aliquots sequentially taken by 300 μL using a PD-10 column.

TABLE 1

| vial | Activity (uCi/300 μL) |
|---|---|
| 1 | 2 |
| 2 | 0 |

TABLE 1-continued

| vial | Activity (uCi/300 μL) |
|---|---|
| 3 | 55 |
| 4 | 114 |
| 5 | 990 |
| 6 | 4100 |
| 7 | 8400 |
| 8 | 8410 |
| 9 | 4700 |
| 10 | 2900 |
| 11 | 640 |
| 12 | 180 |

<Experimental Example 1> Identification of Neovascular-Targeting Contrast Medium Labeling Ability For the $^{18}$F-nanobody prepared in Example 1, a radiochemical yield was identified using Radio-TLC. The results are shown in FIG. 1.

Figure 1:
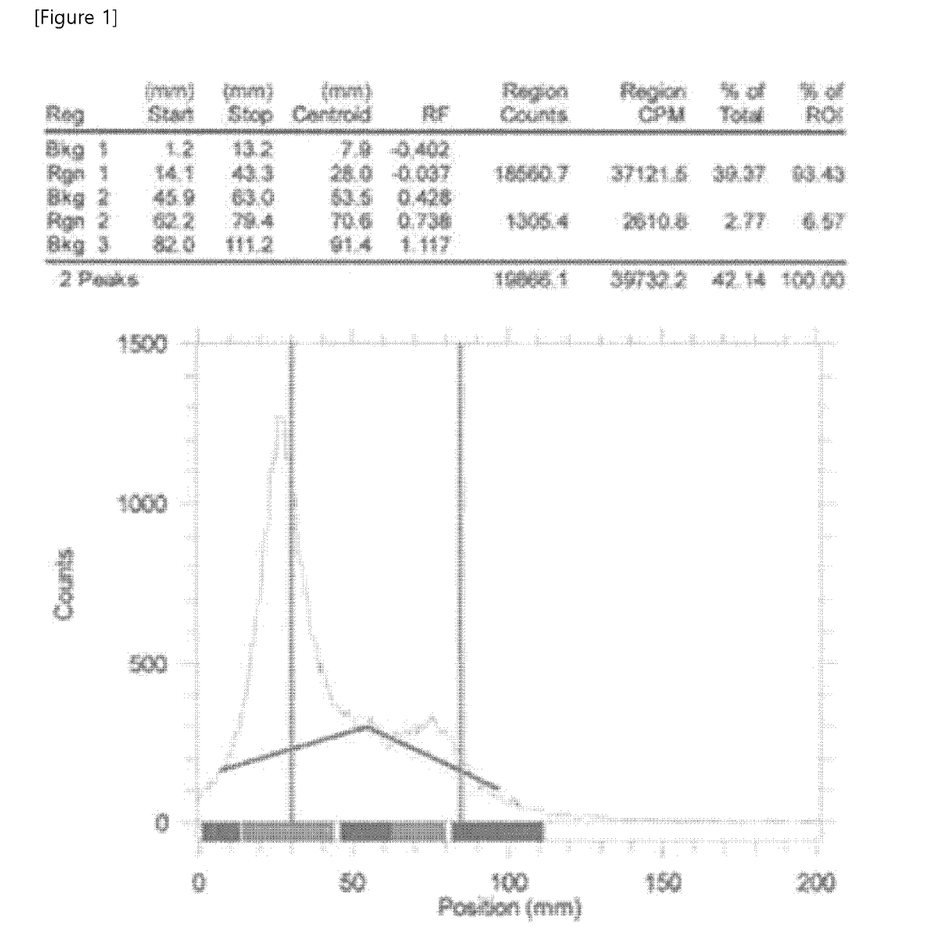
FIG. 1 is the result of identifying a radiochemical yield of the neovascular-targeting contrast medium.

As shown in FIG. 1, when 2,3,5,6-tetrafluorophenyl-6-[$^{18}$F]-fluoronicotinate and the nanobody reacted with each other at room temperature for 10 minutes, the radiochemical yield was greater than or equal to 93%.

<Experimental Example 2> Identification of $\alpha_v\beta_3$ Integrin Targeting Effect of $^{18}$F-Nanobody Targeting Angiogenesis According to the Present Disclosure in Tumor Site In order to identify the contrast effect of the contrast medium composition according to the present disclosure as prepared in the Example 1 in the tumor mouse animal model, the following experiment was performed.

The $\alpha_v\beta_3$ integrin targeting effect was identified using $^{18}$F-cRGDfk as a positive control.

Specifically, an animal model was produced by xenografting (inoculation) U87-MG cells into Athymic nude mice (female, 6-8 weeks old). When the tumor grew to a size of 0.8 cm to 1 cm, the contrast medium was injected into the tail vein (1 mg/kg) to analyze the contrast effect over time. The results are shown in FIG. 2 and FIG. 3.

Figure 2:
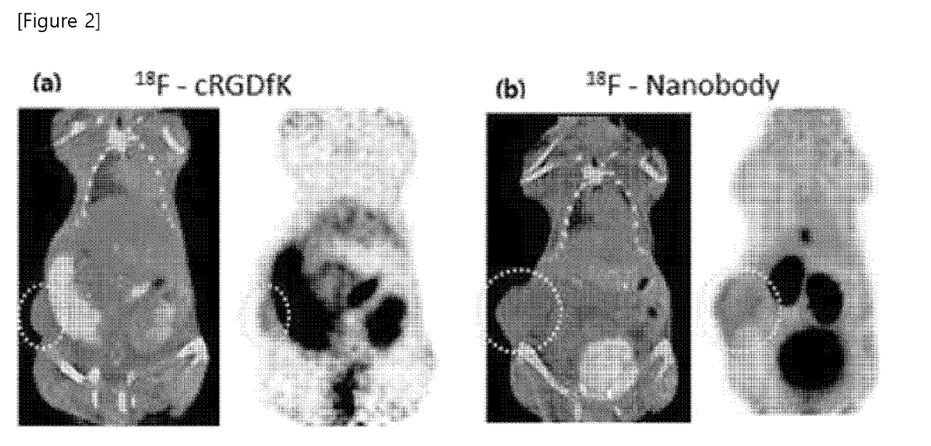
FIG. 2 is a diagram showing the results of identifying the $\alpha_v\beta_3$ integrin targeting effects of the neovascular-targeting contrast medium according to the present disclosure and of a positive control ($^{18}$F-cRGDfk) at the tumor site.

As shown in FIG. 2, it was identified that at 1 hour after intravenous injection of $^{18}$F-cRGDfk or $^{18}$F-nanobody, PET image signals were expressed at the tumor sites of the mice of both groups. It was identified that the tumor site of the mouse injected with $^{18}$F-nanobody exhibited a clearer image signal than that of the mouse injected with $^{18}$F-cRGDfk.

Figure 3:
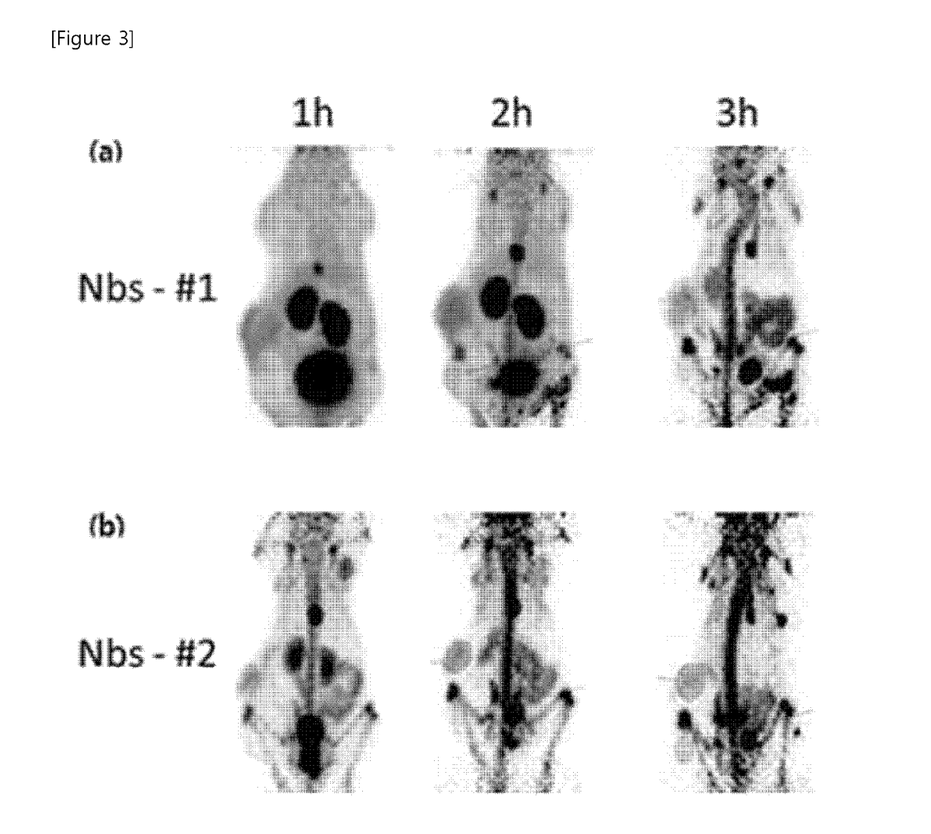
FIG. 3 is a diagram showing the results of identifying the $\alpha_v\beta_3$ integrin targeting effect of the neovascular-targeting contrast medium according to the present disclosure at the tumor site.

As shown in FIG. 3, it was identified that the location of the mouse tumor was accurately indicated for 1 hour, 2 hours and 3 hours after injection of $^{18}$F-nanobody.

The preferred examples of the present disclosure have been described. Those of ordinary skill in the technical field to which the present disclosure belongs will be able to understand that the present disclosure may be implemented in a modified form within a range that does not deviate from the essential characteristics of the present disclosure. Therefore, the disclosed Examples should be considered not in a limiting manner but in an illustrative manner. The scope of the present disclosure is indicated in the claims, not the foregoing description. Any changes within the equivalent scope thereof are included in the present disclosure.

The invention claimed is:

1. A neovascular-targeting contrast medium composition comprising:
    an $α_vβ_3$ integrin targeting nanobody encoded by at least one kind of base sequence selected from a group consisting of base sequences represented by SEQ ID NOs: 1 to 10; and
    a probe labeled with a radioactive isotope.

2. The neovascular-targeting contrast medium composition of claim 1, wherein the base sequence represented by SEQ ID NO: 1 encodes an amino acid sequence of the nanobody represented by SEQ ID NO: 11,
    a base sequence represented by SEQ ID NO: 2 encodes an amino acid sequence thereof represented by SEQ ID NO: 12, and
    a base sequence represented by SEQ ID NO: 3 encodes an amino acid sequence thereof represented by SEQ ID NO: 13.

3. The neovascular-targeting contrast medium composition of claim 1, wherein the nanobody includes a variable region of a heavy chain antibody (VHH) derived from Camelidae.

4. The neovascular-targeting contrast medium composition of claim 1, wherein in the probe labeled with the radioactive isotope, the radioactive isotope includes one of C-11, N-13, O-15, F-18, Ru-82, Ga-68, Cu-60, Cu-61, Cu-62, Cu-64, Cu-67, K-38, Rb-82, Sc-44, I-123, I-124, I-125, Zr-89, Y-86, Y-90, Lu-177, In-111 or Tc-99m.

5. The neovascular-targeting contrast medium composition of claim 4, wherein the probe labeled with the radioactive isotope includes a compound represented by a following Chemical Formula 1:

Chemical Formula 1

(wherein in the Chemical Formula 1, each of $R^1$ to $R^5$ represents hydrogen or halogen, $R^6$ represents C-11, N-13, O-15, F-18, Ru-82, Ga-68, Cu-60, Cu-61, Cu-62, Cu-64, Cu-67, K-38, Rb-82, Sc-44, I-123, I-124, I-125, Zr-89, Y-86, Y-90, Lu-177, In-111 or Tc-99m.

6. The neovascular-targeting contrast medium composition of claim 5, wherein the radioactive isotope-labeled probe includes a compound represented by a following Chemical Formula 2:

Chemical Formula 2

7. The neovascular-targeting contrast medium composition of claim 1, wherein the contrast medium composition is used for positron emission tomography (PET) imaging, computed tomography (CT) imaging, single-photon emission computed tomography (SPEC) imaging, PET/CT imaging, PET/MRI imaging, or PET/optical imaging, and PET/MR/optical imaging.

8. A method for diagnosing angiogenesis-related diseases, comprising:
   administering the neovascular-targeting contrast medium composition of claim 1 to a subject; and
   determining a presence of the angiogenesis-related diseases in the subject based on an image signal.

9. The method claim 8, wherein the angiogenesis-related disease includes at least one kind selected from a group consisting of arteriosclerosis, cancer, diabetic retinopathy, angiogenesis glaucoma, posterior lens fibrosis, proliferative vitreous retinopathy, immature retinopathy, ophthalmic inflammation, corneal ulcer, conical cornea, macular degeneration, Sjogren's syndrome, myopic tumor, corneal graft rejection, abnormal wound union, trachoma, bone disease, rheumatoid arthritis, osteoarthritis, septicemia arthritis, hemangiomas, angiofibroma, psoriasis, pyogenic granuloma, proteinuria, abdominal aortic aneurysm disease, degenerative cartilage loss due to traumatic joint damage, neuro demyelination disease, liver cirrhosis, glomerular disease, immature rupture of the embryonic membrane, inflammatory bowel disease, periodontal ligament disease, restenosis, inflammation of the central nervous system, Alzheimer's disease, skin aging, thyroid hyperplasia, and Grave's disease.

10. A method for diagnosing cancers, comprising:
    administering the neovascular-targeting contrast medium composition of claim 1 to a subject, and
    determining a presence of the angiogenesis-related diseases in the subject based on an image signal.

11. The method of claim 10, wherein the cancer includes at least one kind selected from a group consisting of skin cancer, prostate cancer, breast cancer, cervical cancer, colon cancer, lung cancer, gallbladder cancer, pancreatic cancer, gastric cancer, ovarian cancer, malignant melanoma, malignant lymphoma, thyroid cancer, metastatic brain tumor and brain glioma.

12. A method for preparing a neovascular-targeting contrast medium, the method comprising:
    step 1 of reacting an $\alpha_v\beta_3$ integrin targeting nanobody encoded by at least one kind of base sequence selected from a group consisting of base sequences represented by SEQ ID NOs: 1 to 10 with a probe labeled with a radioactive isotope in a buffer solution at pH 8.0 or higher:

Reaction Formula 1

(wherein in the Reaction Formula 1, each of $R^1$ to $R^5$ represents hydrogen or halogen, $R^6$ represents C-11, N-13, O-15, F-18, Ru-82, Ga-68, Cu-60, Cu-61, Cu-62, Cu-64, Cu-67, K-38, Rb-82, Sc-44, I-123, I-124, I-125, Zr-89, Y-86, Y-90, Lu-177, In-111 or Tc-99m.

* * * * *